United States Patent [19]
Koch et al.

[11] Patent Number: 6,153,175
[45] Date of Patent: Nov. 28, 2000

[54] INDANYLIDENE COMPOUNDS, A PROCESS FOR THEIR PREPARATION AND THEIR USE AS UV ABSORBERS

[75] Inventors: Oskar Koch, Göttingen; Horst Surburg, Holzminden; Roland Langner, Bevern; Horst Sommer, Holzminden, all of Germany

[73] Assignee: Haarmann & Reimer GmbH, Holzminden, Germany

[21] Appl. No.: 09/238,287

[22] Filed: Jan. 28, 1999

Related U.S. Application Data

[62] Division of application No. 08/905,258, Aug. 1, 1997, Pat. No. 5,965,066.

[30] Foreign Application Priority Data

Aug. 7, 1996 [DE] Germany .................. 196 31 863

[51] Int. Cl.[7] .................. A61K 7/42; C07C 255/03
[52] U.S. Cl. .................. 424/59; 424/70.9; 558/426; 558/427
[58] Field of Search .................. 558/426, 427; 514/520; 424/59, 70.9

[56] References Cited

U.S. PATENT DOCUMENTS

| | | | |
|---|---|---|---|
| 3,751,563 | 8/1973 | Richardson | 424/60 |
| 4,284,621 | 8/1981 | Preuss et al. | 424/59 |
| 4,307,108 | 12/1981 | Belletire et al. | 424/274 |
| 4,617,390 | 10/1986 | Hoppe et al. | 544/197 |
| 5,563,298 | 10/1996 | Weitzel et al. | 568/632 |

FOREIGN PATENT DOCUMENTS

| | | | |
|---|---|---|---|
| 2816819 | 10/1979 | Germany | A61K 7/42 |
| 4-134043 | 5/1992 | Japan | C07C 49/747 |

OTHER PUBLICATIONS

Arthur C. Cope et al.: "The Rearrangement of Allyl Groups in Three–carbon Systems. V. Ethyl(3–indenyl)–allylcyanoacetate". Journal of the American Chemical Society., Bd. 71, Nr. 5, May 19, 1949, pp. 1589–1593.

E.C. Horning et al.: "Dimethoxyindanyl and –indenyl Derivatives". Journal of the American Chemical Society, Bd. 76, Nr. 6, Mar. 30, 1954, pp. 1700–1702.

A.K. Bahl et al.: "Nuclear Magnetic Resonance Evidence Regarding the Stereochemistry of Some Cyanoindanylidene Compounds". Journal of the Chemical Society, Section C: Organic Chemistry., 1971, pp. 1583–1585.

E. Campaigne et al.: "Ring closure of Yidenemalonitriles. II. Steric Effects of a Ring at the beta–Position". Journal of Organic Chemistry, Bd. 28, Nr. 3, Mar. 22, 1963, pp. 623–624.

Richard Sommerville: "Synthesis and Pharmacological Ealuation of Aromatic Dihydroxylated Spiro[indan–1, 3'–pyrrolidine] and Spiro [indan–2,2'–pyrrolidine] Derivatives". Journal of Pharmaceutical Sciences, Bd. 74, Nr. 5, May 5, 1985, pp. 553–555.

Joseph H. Chan et al.: "2,4–Diamino–5–benzylpyrimidines as Antibacterial Agents. 14 2,3–dihydro–1–(2,4–diamino–5–pyrimidyl)–1H–indenes as Conformationally Restricted Analogues of Trimethoprim" Journal of Medicinal Chemistry, Bd. 334, Nr. 2, Feb., 1991, pp. 550–555.

Swati Das et al.: "Aryl Participated Cyclisations Involving Indane Derivatives A Total Synthesis of (+/–)–isolongifolene" Tetrahedron Letters, Bd. 33, Nr. 9, Feb. 25, 1992, pp. 1229–1232.

N.F. Eweiss et al.: Knoevenagel–Tyoe Condensation of Indan–1–one with Active Methylene Compounds. Revue Roumaine De Chemie, Bd. 24, Nr. 11–12, 1979, pp. 1485–1489.

Basudeb Basu et al.: "Studies on Intramolecular Cyclisatins. Synthesis of ring systems Related to Sesquiterpenes". Synthetic Communications, Bd. 11, Nr. 10, 1981, pp. 9033–809.

Sukanta Bhattacharyya et al.: "Selective Reduction of Dienones. Intermediates for Sesqui– and diterpenes". Synthetic Communications, Bd. 19, Nr. 3 and 4, 1989, pp. 673–678.

M.. Aadil et al.: Synthesis of 4,5 Disubstitued 2–Chloronicotinates. Synthetic Communications, Bd. 23, Nr. 18, 1993, pp. 2587–2592.

Database WPI, Section Ch, Week 9225 Derwent Publications Ltd., London, GB; class D21, AN 92–204486 & JP 04 134 043 (Kao Corp.) May 7, 1992.

Organikum, pp. 458–461, (1986).

B.L. Diffey, et al.: "A new substrate to measure sunscreen protection factors throughout the ultraviolet spectrum", J. Soc. Cosmet. Chem., 40, (3), pp. 127 –133 (1989).

*Primary Examiner*—Floyd D. Higel
*Assistant Examiner*—Ebenezer Sackey
*Attorney, Agent, or Firm*—Norris, McLaughlin & Marcus, P.A.

[57] ABSTRACT

Compounds of the formula I according to claim 1 are excellently suitable as UV absorbers for use in cosmetic products, in particular sunscreen compositions, daytime care products and hair care products. They are furthermore suitable for protection of products.

2 Claims, No Drawings

INDANYLIDENE COMPOUNDS, A PROCESS FOR THEIR PREPARATION AND THEIR USE AS UV ABSORBERS

This application is a divisional of Ser. No. 08/905,258 filed Aug. 1, 1997 now U.S. Pat. No. 5,965,066.

The invention relates to new indanylidene compounds, a process for their preparation and their use as UV absorbers, for example in cosmetic compositions, in particular in sunscreen compositions, daytime care products and hair care products, and also for improving the stability of industrial products, such as paints, varnishes, plastics, textiles, packaging materials and rubbers, to light.

Depending on their wavelength, UV rays are called UV-A rays (320–400 nm, UV-A-I: 340–400 nm, UV-A-II: 320–340 nm) or UV-B rays (280–320 ni). Quite generally, the damaging effect of UV rays on the human skin increases as the wavelength decreases and the duration of exposure increases.

UV rays can thus cause skin damage, it being possible for the UV-B radiation to cause sunburn (erythema) up to extremely severe skin burns. Very frequent and unprotected irradiation of the skin with sunlight also leads to a loss in elasticity of the skin and to increased formation of wrinkles, and overall to premature ageing of the skin. In extreme cases, pathological skin changes up to skin cancer may occur.

UV-A radiation has the effect of rapid, weak direct pigmentation of the skin. UV-A rays penetrate into the lower layers of the skin and can accelerate the ageing process of the skin there. The shorter wavelength UV-A-II radiation assists the development of sunburn. UV-A radiation can furthermore trigger phototoxic or photoallergic skin reactions. Confirmed relationships between UV-A exposure and an increased risk of skin cancer exist.

Depending on the position of their absorption maxima, UV absorbers for cosmetic and pharmacological preparations are classified into UV-A and UV-B absorbers; if both UV-A and UV-B are absorbed by one UV absorber, a UV-A/B broadband absorber is referred to in this case.

The most diverse compounds have already been proposed as UV absorbers, such as octyltriazone (DE-A 3 206 398), 2-hydroxy-4-methoxybenzophenone (U.S. Pat. No. 3,751,563) and 4-tert-butyl-4'-methoxy-dibenzoylmethane (DE-A 2 945 925). These compounds either do not have the desired broad UV-A and UV-B absorption, or have only a low absorption in this range or are not sufficiently photostable.

The invention is therefore based on the object of providing improved UV-A and UV-B broadband absorbers.

The invention relates to the use of compounds of the formula (I)

wherein
R' to $R^4$, $R^{3'}$, $R^{3''}$, $R^{4'}$ and $R^{4''}$ independently of one another denote hydrogen, $C_1$–$C_8$-alkyl or $C_5$–$C_{10}$-cycloalkyl, with the proviso that two substituents on adjacent C atoms together can also denote an optionally substituted $C_1$–$C_4$-alkylene group, in particular $C_3$–$C_4$-alkylene, wherein a methylene group can be replaced by —O—, —S— or —NH—, and furthermore independently of one another denote $C_1$–$C_4$-alkoxy, hydroxyl, carboxyl, carbalkoxy or carbamoyl, $R^5$ to $R^8$ independently of one another have the meaning of $R^1$, $R^2$ or sulpho or aminosulphonyl, X and Y independently of one another denote CN, $CO_2R^9$, $CO_2NR^9R^{10}$ or $COR^9$, wherein $R^9$ and $R^{10}$ independently of one another represent hydrogen, $C_1$ to $C_8$-alkyl or $C_5$–$C_{10}$-cycloalkyl, and furthermore one of the radicals X or Y can additionally denote a $C_1$–$C_8$-alkyl radical, a $C_5$–$C_{10}$-aryl radical, in particular phenyl, or a 5- to 6-membered heteroaryl radical which contains 1 or 2 heteroatoms from the series consisting of N, O and S, or X and Y, together with the β atom to which they are bonded, denote a 5- to 7-membered ring which contains up to 3 heteroatoms, in particular oxygen and/or nitrogen, it being possible for the ring atoms to be substituted, in particular by exocyclically double-bonded oxygen (keto group), preferably in the adjacent position to the β atom, and n and m independently of one another denote zero or 1, as UV absorbers, preferably in sunscreen compositions.

Compounds of the formula wherein
$R_1$, $R_2$ and $R_3$ in each case independently of one another can be identical or different and denote a hydrogen atom, halogen atom, hydroxyl group, nitro group, cyano group or monovalent, optionally substituted organic radical and $R_4$ denotes a hydrogen atom, halogen atom, nitro group, cyano group or monovalent, optionally substituted organic radical and $R_5$ can be identical or different and denotes a halogen atom, hydroxyl group, nitro group, cyano group or monovalent, optionally substituted organic radical, are known from EP-A 670 298.

The invention therefore also relates to compounds of the formula (I) with the exception of the compounds mentioned in EP-A 670 298.

The invention preferably relates to compounds of the formula (1) wherein

X and Y are not an unsubstituted or substituted phenyl ring if m=n=zero.

The properties of the compounds I can be varied within wide limits by suitable choice of the substituents. This particularly applies both to the position of the absorption maximum (thus, for example, in the case where $R^6$=alkoxy, the maximum lies in the UV-A range, and if $R^5$–$R^8$=H and n, m=0 and $R^1$–$R^4$=H, the maximum lies in the UV-B range, and in the case where $R^7$=alkyl, the UV-A and the UV-B range are even covered) and to the water- and oil-solubility (sulphonic acid groups in the aromatic ring promote water-solubility, and in the absence of sulphonic acid groups the compounds I are chiefly oil-soluble).

Preferred compounds are those in which X denotes cyano and Y denotes carbo-$C_1$–$C_4$-alkoxy. Compounds which are furthermore preferred are those in which $R^6$ denotes alkyl or, in particular, alkoxy; they have a high extinction. The preferred compounds I correspond to the formulae

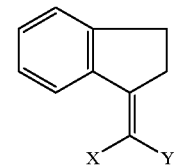

(Ia)

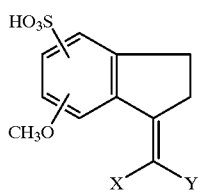

(Ib)

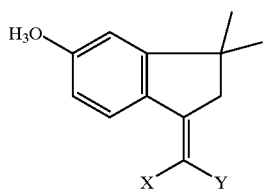

(Ic)

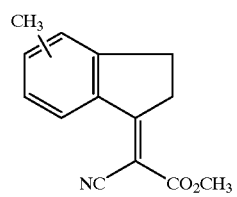

(Id)

The compounds according to the invention are particularly suitable for use in sunscreen compositions, preferably in cosmetic and pharmaceutical preparations, but also as anti-ageing agents for industrial products. They are distinguished by an excellent stability to light.

The compounds (I) can be prepared by (Knoevenagel) condensation of compounds of the formula

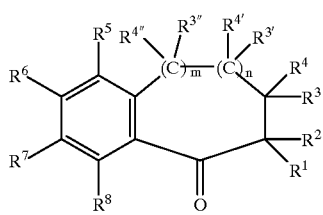

(II)

wherein $R^1$ to $R^8$ have the abovementioned meanings, with compounds of the formula

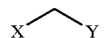

(III)

with the abovementioned meanings for X and Y
(cf. Organikum, VEB Deutscher Verlag, Berlin 1986, page 459) and are to be obtained with good to very good yields.

The indanones used for this can be prepared by F.C. reaction of (substituted) acrylic acid esters with (substituted) aromatics or, in the case of hydroxy substituents ($R^5$–$R^8$), by Fies rearrangement of corresponding phenol esters.

The UV absorbers of the formula (I) according to the invention have a fortunate combination of desirable properties, in particular
high UV protection at only low use concentrations,
excellent stability to light,
excellent heat stability,
good solubility in solvents for cosmetics and excellent solubility of the crystalline, oil-soluble UV absorbers in liquid, oil-soluble absorbers such as ethyl, isoamyl and isooctyl p-methoxycinnamate, ethylhexyl salicylate, homomenthyl salicylate, menthyl anthranilate, ethylhexyl p-aminobenzoate and ethyl and ethylhexyl 3,3-diphenyl-2-cyanoacrylate, or combinations of liquid, oil-soluble UV absorbers,
compatibility with cosmetic bases,
pH stability,
problem-free processability in cosmetic formulations and stability under use conditions,
compatibility with packaging materials,
no discoloration of textiles, or stains can be washed out without problems,
colourlessness and odour neutrality,
waterproof UV protection.

The compounds according to the invention can be used in cosmetic or pharmaceutical formulations as UV broadband absorbers which prevent passage of UV rays through the film of formulation applied. This is in general the case if the cosmetic or pharmaceutical formulations comprise 0.5 to 15, preferably 1 to 10, in particular 2 to 7% by weight (based on the total weight of the formulation) of the compounds according to the invention.

The formulations comprising the compounds according to the invention can be used for protecting the skin and hair—especially hair already predamaged by permanent waving, colouring and bleaching—against UV irradiation. These cosmetic and pharmaceutical formulations used to protect the skin from UV radiation can be present in the use forms usually used, i.e. as an oil-in-water or water-in-oil emulsion, as a milk or as a lotion or cream, aqueous or aqueous-alcoholic gel or lotion, aerosol, hydrodispersion gel (emulsifier-free) or any other customary cosmetic or pharmaceutical formulation. For protection of the hair against UV rays, formulations as a shampoo, rinse, treatment course, gel, lotion, spray or cream are preferably used.

The cosmetic and pharmaceutical formulations can comprise the constituents usually used in these compositions, such as, for example, emulsifiers, surface-active compounds, lanolin, vaseline, water, triglycerides of fatty acids, polyethylene glycols, fatty alcohols, ethoxylated fatty alcohols, fatty acid esters (for example isopropyl palmitate, isooctyl stearate, diisopropyl adipate and the like), naturally occurring or synthetic oils or waxes, pigments (for example titanium dioxide, zinc oxide, pearlescent pigments, coloured pigments), thickeners (for example hydroxyethylcellulose, bentonite and the like), preservatives, moisturizing agents, vitamins, silicone oils, glycerol, ethyl alcohol and perfume oils.

The compounds according to the invention can be employed in the corresponding formulations individually or as a mixture; they can also be employed in combination with UV absorbers of other classes of substance. Examples of such compounds include
p-aminobenzoic acid
ethyl p-aminobenzoate, ethoxylated (25 mol)
2-ethylhexyl p-dimethylaminobenzoate
ethyl p-aminobenzoate, N-propoxylated (2 mol)
glycerol p-aminobenzoate
homomenthyl salicylate
2-ethylhexyl salicylate
triethanolamine salicylate
4-isopropylbenzyl salicylate
menthyl anthranilate
ethyl diisopropylcinnamate
2-ethylhexyl p-methoxycinnamate
methyl diisopropylcinnamate
isoamyl p-methoxycinnamate
p-methoxycinnamic acid diethanolamine salt
isopropyl p-methoxycinnamate
2-ethylhexyl 2-cyano-3,3-diphenylacrylate
ethyl 2-cyano-3,3'-diphenylacrylate
2-phenylbenzimidazolesulphonic acid and salts
3-(4'-trimethylanmmonium)benzylidene-bornan-2-one methylsulphate
terephthalylidene-dibornanesulphonic acid and salts
4-t-butyl-4'-methoxy-dibenzoylmethane
β-imidazole-4(5)-acrylic acid (urocaninic acid)
2-hydroxy-4-methoxybenzophenone
2-hydroxy-4-methoxybenzophenone-5-sulphonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methylbenzophenone
3-(4'-sulpho)benzylidene-bornan-2-one and salts
3-(4'-methylbenzylidene)-d,l-camphor
3-benzylidene-d,l-camphor
4-isopropyldibenzoylmethane
2,4,6-trianilino-(p-carbo-2'-ethylhexyl-1'-oxy)-1,3,5-triazine
phenylene-bis-benzimidazyl-tetrasulphonic acid disodium salt
N-[(2 and 4)-[2-(oxoborn-3-ylidene)methyl]benzyl] acrylamide polymer.

Particularly suitable UV absorbers are:
2-ethylhexyl p-methoxycinnamate,
isoamyl p-methoxycinnamate,
2-phenylbenzimidazolesulphonic acid,
3-(4'-methylbenzylidene)-d,l-camphor,
2-ethylhexyl 2-cyano-3,3-diphenylacrylate,
2-ethylhexyl salicylate,
4-tert-butyl-4'-methoxydibenzoylmethane and
phenylene-bis-benzimidazyl-tetrasulphonic acid disodium salt.

Combination of the compounds I with finely divided pigments, such as, for example, titanium dioxide, zinc oxide and iron oxide, in sunscreen and daytime care products with UV protection is also possible.

The compounds according to the invention are also particulary suitable for photostabilization of UV absorbers of low stability to UV light. Photostabilization of the dibenzoylmethane compounds, which are very unstable to light, is particularly successful.

A light-stable UV filter combination for protecting human skin against UV rays in the range of 280–380 nm in cosmetic products is achieved by employing 1 to 5% by weight of, for example, 4-tert-butyl-4'-methoxydibenzoylmethane and at least 1% by weight of the compound according to formula 1, preferably in a ratio of 2–4 parts of the compound according to formula I to 1 part of tert-butylmethoxydibenzoylmethane. The molar ratio should be 1 or higher.

Another light-stable UV filter combination is achieved by employing 1–10% by weight of ethylhexyl or isoamyl p-methoxycinnamate with at least 1% by weight of the compound of the formula 1, preferably in a ratio of 1:1. The molar ratio should be 0.8 or higher.

Combinations of p-methoxycinnamic acid esters and dibenzoylmethane derivatives and compounds of the formula I can be formulated in a light-stable form by employing, for example, 1–5% by weight of 4-tert-butyl-4'-methoxydibenzoylmethane, 1–10% by weight of ethylhexyl or isoamyl p-methoxycinnamate and at least 2% by weight of the compounds of the formula I, preferably in a ratio of 1 part of dibenzoylmethane derivative, 2 parts of p-methoxycinnamic acid ester and 2 parts of the compound of the formula I.

A further, very photostable UV absorber, such as, for example, methylbenzylidene-camphor, 2-ethylhexyl 2-cyano-3,3'-diphenylacrylate or octyltriazone, is further advantageously to be added to this three-component combination.

The compounds according to the invention can furthermore also be combined with UV absorbers which are employed for protection of industrial products. Examples of such UV absorbers are compounds from the series consisting of benzotriazoles, benzophenones, triazines, cinnamic acid esters and oxalanilides.

EXAMPLES

Example 1

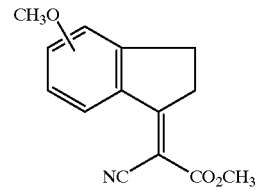

32 g (0.2 mol) of 5-methoxy-1-indanone, 20 g (0.2 mol) of methyl cyanoacetate, 17 g of proplonic acid and 2 g of ammonium acetate are mixed and the mixture is heated at 120° C. for 5 hours. After cooling to room temperature, the crude product is recrystallized from methanol. Yield: 60% of theory; $E^{1/1}$ 1268 ($\lambda_{max}$ 345 nm).

Example 2

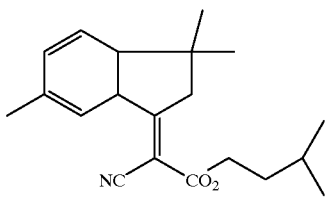

3,3,6-Trimethyl-1-indanone and isoamyl cyanoacetate are reacted analogously to Example 1. Yield: 70% of theory; $E^{1/1}$ 566 ($\lambda_{max}$ 332 nm)/$E^{1/1}$ 551 ($\lambda_{max}$ 309 nm).

Example 3

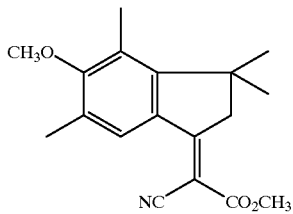

3,3,4,6-Tetramethyl-5-methoxy-1-indanone and methyl cyanoacetate are reacted analogously to Example 1. Yield: 70% of theory; $E^{1/1}$ 800 ($\lambda$338 nm).

Example 4

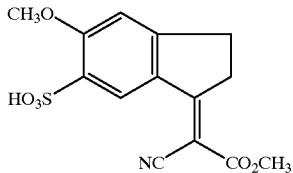

0.1 mol of the compound from Example 1 is heated at 70 to 80° C. in a mixture of 0.2 mol of acetic anhydride and 0.2 mol of concentrated sulphuric acid for 30 minutes. After cooling to room temperature, isopropanol is added to the reaction mixture and the product which has then precipitated out is filtered off with suction and dried. Yield: 70% of theory; $E^{1/1}$ 800 ($\lambda_{max}$ 345 nm).

Components used

| Trade name | Chemical name | Supplier |
| --- | --- | --- |
| Abil 100 | Polydimethylsiloxane | 7 |
| Antaron V-216 | Vinylpyrrolidone/hexadecene copolymer | 18 |
| Arlacel 1689 | Sorbitan monooleate/propylglyceryl 3-ricinoleate | 4 |
| Arlacel 165 | Glycerol stearate/polyethylene glycol (MW 100) stearate mixture | 4 |
| Arlatone 983 S | Polyethylene glycol (MW 5) glyceryl stearate | 4 |
| Arlatone G | hardened with 25 mol of ethylene oxide | 4 |
| Baysilone Fluid PK 20 | Silicone oil | 5 |
| Betone Gel MIO | Mineral oil, quatemium-18 hectorite, propylene carbonate | 17 |
| Brij 76 | Polyethylene glycol (MW 10) stearyl ether | 4 |
| Carbopol 2984 | Polyacrylic acid | 2 |
| Carbopol 954 | Polyacrylic acid | 2 |
| Cetiol HE | Polyol-fatty acid ester | 3 |
| Cetiol OE | Dicaprylyl ether | 3 |
| Cetiol SN | Cetyl/stearyl isononanoate | 3 |
| Copherol F 1250 | D-α-tocopheryl acetate | 3 |
| Cutina CBS | Glycerol stearate, cetyl/stearyl alcohol, cetyl palmitate, coconut glycerides | 3 |
| Dehymuls PG PH | Polyglycerol poly-12-hydroxystearate | 3 |
| Diisopropyl adipate | Adipic acid diisopropyl ester | 3 |
| D-Panthenol | Panthothenyl alcohol | 15 |
| EDTA B. liq. | Tetrasodiumethylenediamine-tetraacetate | 6 |
| Eusolex TA | Titanium dioxide | 13 |
| Eutanol G | 2-Octyldodecanol | 3 |
| Eumulgin B2 | Cetyl/stearyl alcohol, etherified with 20 mol of ethylene oxide | 3 |
| Finsolv TN | Alkylbenzoate | 23 |
| Genapol LRO liq. | Polyethylene glycol (MW 5) glyceryl stearate | 9 |
| Glycerol | 1,2,3-Propane triol | 3 |
| Isopropyl myristate | Myristic acid isopropyl ester | 3 |
| Jojoba oil | Jojoba oil | 19 |
| Lameform TGI | Triglycerol diisostearate | 3 |
| Lamepon S | Protein/coconut fatty acid condensate, potassium salt | 3 |
| Lanette O | Cetyl/stearyl alcohol mixture | 3 |
| Macadamia nut oil | Macadamia nut oil | 20 |
| Myritol 318 | Caprylic/capric triglyceride | 3 |
| Natrosol 250 HHR | Hydroxyethylcellulose | 11 |
| NEO HELIOPAN ® AV | Isooctyl p-methoxycinnamate | 1 |
| NEO HELIOPAN ® BB | 2-Hydroxy-4-methoxybenzophenone | 1 |
| NEO HELIOPAN ® E1000 | Isoamyl p-methoxycinnamate | 1 |
| NEO HELIOPAN ® HYDRO | Phenylbenzimidazolesulphonic acid | 1 |
| NEO HELIOPAN ® MBC | 3-(4-Methylbenzylidene)-d,1-camphor | 1 |
| NEO HELIOPAN ® OS | 1-Ethylhexyl salicytate | 1 |
| NEO HELIOPAN ® 303 | Isooctyl α-phenyl-β-cyano-cinnamate | 1 |
| Olive oil | Olive oil | 21 |
| Parsol 1789 | Butylmethoxydibenzoylmethane | 12 |
| Permulgin 2550 | Wax | 14 |
| Permulgin 3220 | Wax | 14 |
| Permulen TR 1 | Polyacrylate | 2 |
| Phenonip | Mixture of p-hydroxybenzoic acid esters and phenoxyethanol | 8 |
| Polymer JR 400 | Polyquaternium-10 | 21 |
| 1,2-Propylene glycol | 1,2-Propanediol | 6 |
| Texapon MG 3 | Magnesium lauryl sulphate/disodium lauryl sulphosuccinate | 3 |
| Tocopherol oil | Soya oil with D-α-tocopherol | 22 |
| Uvinul T 150 | Isooctyl triazinyl-p-aminobenzoate | 6 |
| Veegum Ultra | Magnesium aluminium silicate | 10 |
| ZINC OXIDE NEUTRAL H&R | Zinc oxide | 1 |
| Zinc stearate | Zinc stearate | 16 |

Suppliers

1. Haarmann & Reimer GmbH., Holzminden
2. B. F. Goodrich Company, Neuss
3. Henkel KGaA, Düsseldorf
4. ICI Speciality Chemicals, Frankfurt
5. Bayer AG, Leverkusen
6. BASF, Ludwigshafen
7. Godschmidt AG, Essen
8. Nipa Lab. Ltd., Pontypridd, Mid Glam., Wales/GB
9. Hoechst AG, Frankfurt
10. R. T. Vanderbilt Company Inc., Norwalk/USA -continued 11. Hercules Inc., Wilmington, Delaware/USA
12. Hoffmann-LaRoche, Basle/CH
13. E. Merck, Darmstadt
14. Koster Keunen Holland BV, Bladl/NL
15. Akzo Chemie GmbH, Duren
16. Chemische Werke Barlocher, Munich
17. Rheox Inc., Hightstown, New Jersey/USA
18. ISP Global Technologies Deutschland GmbH, Frechen
19. Henry Lamotte, Bremen
20. Erhard Wagner GmbH, Bremen
21. Nordmann & Rassmann GmbH & Co., Hamburg
22. Richter GmbH, Berlin
23. Witco Surfactants GmbH, Steinau a.d. Straβe

Example 5
Sunscreen lotion (O/W)

| CONSTITUENTS | % |
| --- | --- |
| A) Arlatone 983 S | 1.75 |
| Brij 76 | 1.25 |
| Lanette O | 1.15 |
| Myritol 318 | 5.00 |
| Eutanol G | 6.00 |
| Cetiol SN | 6.00 |
| Phenonip | 0.20 |
| UV absorber according to formula (I) | 3.00 |
| B) Distilled water | 46.65 |
| 1,2-Propylene glycol | 2.00 |
| Phenonip | 0.30 |
| C) Distilled water | 25.00 |
| Carbopol 2984 | 0.30 |
| Sodium hydroxide, 10% strength in water | 1.00 |
| D) Perfume oil | 0.40 |
| PREPARATION INSTRUCTIONS: | |

Part A: Melt at about 80° C.
Part B: Heat to about 90° C.,
    add Part B to Part A with stirring.
Part C: Disperse the Carbopol in water without lumps,
    neutralize with sodium hydroxide solution
    to give a gel, add to Part A/B at about 60° C.
    Stir until room temperature is reached.
Part D: Perfume the emulsion at about 30° C.,
    check the pH (6.5 to 7.0).

Example 6
Sunscreen lotion (O/W)

| CONSTITUENTS | % |
| --- | --- |
| A) Arlatone 983 S | 1.75 |
| Brij 76 | 1.25 |
| Lanette O | 1.15 |
| Myritol 318 | 15.00 |
| Cetiol SN | 15.00 |
| Phenonip | 0.20 |
| UV absorber according to formula (I) | 5.00 |
| B) Distilled water | 31.65 |
| 1,2-Propylene glycol | 2.00 |
| Phenonip | 0.30 |
| C) Distilled water | 25.00 |
| Carbopol 2984 | 0.30 |
| Sodium hydroxide, 10% strength in water | 1.00 |
| D) Perfume oil | 0.40 |

PREPARATION INSTRUCTIONS:

Part A: Melt at about 80° C.

-continued

| CONSTITUENTS | % |
| --- | --- |

Part B: Heat to about 90° C.,
    add Part B to Part A with stirring.
Part C: Disperse the Carbopol in water without lumps,
    neutralize with sodium hydroxide solution
    to give a gel, add to Part A/B at about 60° C.
    Stir until room temperature is reached.
Part D: Perfume the emulsion at about 30° C.,
    check the pH (6.5 to 7.0).

Determination of the in-vitro light protection factor in accordance with the method of Diffey and Robson ("A new substrate to measure sunscreen protection factors throughout the ultra violet spectrum", J. Soc. Cosm. Chem. 40 (3), 123–133 (1989)) gave a value of 11.0.

Example 7
Sunscreen milk (W/O)

| CONSTITUENTS | % |
| --- | --- |
| A) Dehymuls PG PH | 5.00 |
| Permulgin 3220 | 0.50 |
| Zinc stearate | 0.50 |
| Myritol 318 | 15.00 |
| Cetiol SN | 15.00 |
| UV absorber according to formula (I) | 5.00 |
| B) Distilled water | 52.50 |
| Glycerol 86% | 5.00 |
| Magnesium sulphate 7 $H_2O$ | 0.50 |
| Phenonip | 0.50 |
| C) Perfume oil | 0.50 |
| PREPARATION INSTRUCTIONS: | |

Part A: Melt carefully at about 90° C.
Part B: Heat to about 95° C.,
    then add Part B to Part A with stirring.
    Stir until room temperature is reached.
Part C: Add Part C at 30° C. and then homogenize Determination of the in-vitro light protection factor in accordance with the method of Diffey and Robson ("A new substrate to measure sunscreen protection factors throughout the ultra violet spectrum", J. Soc. Cosm. Chem. 40 (3), 123–133 (1989)) gave a value of 11.9.

Example 8
Sunscreen lotion (O/W)

| CONSTITUENTS | % |
| --- | --- |
| A) Ariatone 983 S | 1.75 |
| Brij 76 | 1.25 |
| Lanette O | 1.15 |
| Myritol 318 | 15.00 |
| Cetiol SN | 15.00 |
| Finsolv TN | 5.00 |
| Phenonip | 0.20 |
| UV absorber according to formula (I) | 4.00 |
| Parsol 1789 | 1.50 |
| B) Distilled water | 26.15 |
| 1,2-Propylene glycol | 2.00 |
| Phenonip | 0.30 |
| C) Distilled water | 25.00 |
| Carbopol 2984 | 0.30 |
| Sodium hydroxide, 10% strength in water | 1.00 |
| D) Perfume oil | 0.40 |

-continued

| CONSTITUENTS | % |
|---|---|
| PREPARATION INSTRUCTIONS: | |

Part A: Melt at about 80° C.
Part B: Heat to about 90° C.,
    add Part B to Part A with stirring.
Part C: Disperse the Carbopol in water without lumps,
    neutralize with sodium hydroxide solution
    to give a gel, add to Part A/B at about 60° C.
    Stir until room temperature is reached.
Part D: Perfume the emulsion at about 30° C.,
    check the pH (6.5 to 7.0).

Example 9
Sunscreen lotion (O/W)

| CONSTITUENTS | % |
|---|---|
| A) Ariatone 983 S | 1.75 |
| Brij 76 | 1.25 |
| Lanette O | 1.15 |
| Myritol 318 | 12.00 |
| Cetiol SN | 12.00 |
| UV absorber according to formula (I) | 7.00 |
| NEO HELIOPAN ® E 1000 | 7.00 |
| Phenonip | 0.20 |
| B) Distilled water | 28.65 |
| 1,2-Propylene glycol | 2.00 |
| Phenonip | 0.30 |
| C) Distilled water | 25.00 |
| Carbopol 2984 | 0.30 |
| Sodium hydroxide. 10% strength in water | 1.00 |
| D) Perfume oil | 0.40 |
| PREPARATION INSTRUCTIONS: | |

Part A: Melt at about 80° C.
Part B: Heat to about 90° C.,
    add Part B to Part A with stirring.
Part C: Disperse the Carbopol in water without lumps,
    neutralize with sodium hydroxide solution to
    give a gel, add to Part A/B at about 60° C.
    Stir until room, temperature is reached.
Part D: Perfume the emulsion at about 30° C.,
    check the pH (6.5 to 7.0).

Example 10
Sunscreen lotion (O/W)

| CONSTITUENTS | % |
|---|---|
| A) Arlacel 165 | 3.00 |
| Eumulgin B 2 | 1.00 |
| Lanette | 1.00 |
| Myritol 318 | 4.00 |
| Cetiol OE | 2.00 |
| Abil 100 | 1.00 |
| Bentone Gel MIO | 3.00 |
| Cutina CBS | 1.00 |
| Phenonip | 0.20 |
| NEO HELIOPAN ® OS (octyl salicylate) | 3.00 |
| NEO HELIOPAN ® AV (octyl methoxycinnamate) | 5.00 |
| NEO HELIOPAN ® E 1000 (isoamyl p-methoxy-cinnamate) | 5.00 |
| NEO HELIOPAN ® MBC (4-methylbenzylidenecamphor) | 1.00 |
| Eusolex TA | 3.00 |

-continued

| CONSTITUENTS | % |
|---|---|
| UV absorber according to formula (I) | 3.00 |
| B) Distilled water | 45.60 |
| Glycerol. 86% strength | 3.00 |
| Phenonip | 0.30 |
| Veegum Ultra | 1.00 |
| Natrosol 250 HHR | 0.30 |
| NEO HELIOPAN ® HYDRO, employed as a 15% strength solution after neutralization with sodium hydroxide (phenylbenzimidazolesulphonic acid), corresponds to active substance: 2.0% | 13.30 |
| C) Perfume oil | 0.30 |
| PREPARATION INSTRUCTIONS: | |

Part A: Melt at about 80° C.,
    then disperse the Eusolex TA carefully.
Part B: Heat to about 90° C. without the Veegum
    and Natrosol, then disperse the Veegum
    and Natrosol, add Part B to Part A with
    stirring. Stir until room temperature is reached.
Part C: Add Part C at 30° C. and then homogenize.
    Check the pH (7.0–7.5).

Example 11
Sunscreen lotion (W/O)

| CONSTITUENTS | % |
|---|---|
| A) Arlacel 1689 | 3.50 |
| Finsolv TN | 6.00 |
| NEO HELIOPAN ® E 1000 (isoamyl p-methoxy-cinnamate) | 7.00 |
| Uvinul T 150 (octyltriazone) | 1.00 |
| UV absorber according to formula (I) | 3.00 |
| Copherol F 1250 | 2.00 |
| Permulgin 2550 | 1.00 |
| Myritol 318 | 6.00 |
| Cetiol SN | 6.00 |
| ZINC OXIDE NEUTRAL H&R (zinc oxide) | 7.00 |
| B) Distilled water | 51.70 |
| Glycerol 86% | 5.00 |
| Phenonip | 0.50 |
| C) Perfume oil | 0.30 |
| PREPARATION INSTRUCTIONS: | |

Part A: Melt carefully at about 90° C.
    (without ZINC OXIDE NEUTRAL H&R).
    Then disperse ZINC OXIDE NEUTRAL
    H&R carefully.
Part B: Heat to about 95° C.,
    then add Part B to Part A with stirring.
    Stir until room temperature is reached.
Part C: Add Part C at 30° C. and then homogenize.

Example 12
Sunscreen oil

| CONSTITUENTS | % |
|---|---|
| A) NEO HELIOPAN ® E 1000 (isoamyl p-methoxy-cinnamate | 7.50 |
| NEO HELIOPAN ® OS (octyl salicylate) | 5.00 |
| UV absorber according to formula (I) | 3.00 |
| Myritol 318 | 34.70 |
| Diisopropyl adipate | 5.00 |
| Olive oil | 1.00 |

-continued

| CONSTITUENTS | % |
|---|---|
| Jojoba oil | 1.00 |
| Macadamia nut oil | 1.00 |
| Tocopherol oil | 1.00 |
| Isopropyl myristate | 35.00 |
| Antaron V-216 | 5.00 |
| Phenonip | 0.50 |
| Perfume oil | 0.30 |
| PREPARATION INSTRUCTIONS: | |
| Mix all the constituents carefully. | |

Example 13
Sunscreen cream gel

| CONSTITUENTS | % |
|---|---|
| A) Distilled water | 75.35 |
| Phenonip | 0.50 |
| EDTA B liquid | 0.10 |
| B) NEO HELIOPAN ® AV | 7.00 |
| (octyl methoxycinnamate) | |
| NEO HELIOPAN ® 303 (octocrylene) | 3.00 |
| NEO HELIOPAN ® MBC | 1.00 |
| (4-methylbenzylidene-camphor) | |
| UV absorber according to formula (I) | 3.00 |
| Cetiol SN | 5.00 |
| Eutanol G | 3.00 |
| Lameform TG I | 1.00 |
| Perfume oil | 0.30 |
| Permulen TR-1 | 0.25 |
| Carbopol 954 | 0.05 |
| C) Triethanolamine | 0.45 |
| PREPARATION INSTRUCTIONS: | |
| Part A: Dissolve the contents in water. | |
| Part B: Mix all the constituents | |
| (without the Permulen and Carbopol). | |
| Dissolve the NEO HELIOPAN ® MBC | |
| and the UV absorber according to | |
| formula (I) with gentle heating. | |
| Disperse the Carbopol and Permulen. | |
| Then add Part B to Part A and stir | |
| intensively for 45 minutes. | |
| Part C: Add the triethanolamine to Part A/B, | |
| with stirring. Continue to stir | |
| until the product is homogeneous. | |
| Check the pH (about 7.0). | |

Example 14
Hair shampoo

| CONSTITUENTS | % |
|---|---|
| A) Genapol LRO liquid | 18.00 |
| Texapon MG3 | 36.00 |
| Lamepon S | 6.00 |
| Perfume oil | 0.60 |
| Phenonip | 0.50 |
| Arlatone G | 2.00 |
| UV absorber according to formula (I) | 0.50 |
| NEO HELIOPAN ® E 1000 | 1.00 |
| (isoamyl p-methoxycinnamate) | |
| B) Distilled water. | 33.00 |
| Polymer JR 400 | 0.20 |
| D-Panthenol | 1.00 |
| Sodium chloride | 1.00 |
| Sodium hydroxide 10% strength in water | 0.20 |

-continued

| CONSTITUENTS | % |
|---|---|
| PREPARATION INSTRUCTIONS: | |
| Part A: Dissolve the UV absorber in the | |
| NEO HELIOPAN ® E 1000 and | |
| Phenonip with gentle heating, | |
| then add the Arlatone G and | |
| perfume oil and mix thoroughly. | |
| Weigh in the remaining constituents. | |
| Part B: Dissolve the polymer in the water, | |
| with stirring, add the remaining | |
| constituents and dissolve. | |
| Add Part B to Part A and stir | |
| (check the pH, about 5.5). | |

What is claimed is:

1. Compounds of the formula

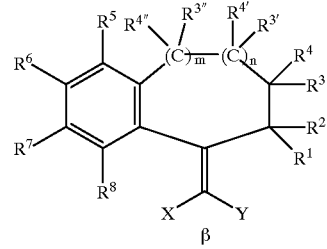

(I)

wherein $R^1$ to $R^4$, $R^{3'}$, $R^{3''}$, $R^{4'}$ and $R^{4''}$ independently of one another denote hydrogen, $C_1$–$C_8$-alkyl or $C_5$–$C_{10}$-cycloalkyl, with the proviso that two substituents on adjacent C atoms together can also denote an optionally substituted $C_1$–$C_4$-alkylene group, in which a methylene group may be replaced by —O—, —S— or —NH—, and furthermore independently of one another denote $C_1$–$C_4$-alkoxy, hydroxyl, carboxyl, carbalkoxy or carbamoyl, $R^5$ to $R^8$ independently of one another have the meaning of $R^1$, $R^2$ or sulpho or aminosulphonyl, X and Y independently of one another denote CN, $CO_2R^9$, $CO_2NR^9R^{10}$ or $COR^9$, wherein $R^9$ and $R^{10}$ independently of one another represent hydrogen, $C_1$ to $C_8$-alkyl or $C_5$–$C_{10}$-cycloalkyl, and furthermore one of the radicals X or Y can additionally denote a $C_1$–$C_8$-alkyl radical, a $C_5$–$C_{10}$-aryl radical, or a 5- to 6-membered heteroaryl radical which contains 1 or 2 heteroatoms selected from the group consisting of N, O and S, or X and Y, together with the β atom to which they are bonded, denote a 5- to 7-membered ring which contains up to 3 heteroatoms selected from the group consisting of oxygen and nitrogen, substituted by exocyclically double-bonded oxygen (keto group) and n and m independently of one another denote zero or 1, with the exception of compounds of the formula

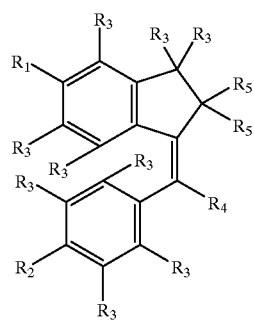

wherein
- $R_1$, $R_2$ and $R_3$ in each case independently of one another can be identical or different and denote a hydrogen atom, halogen atom, hydroxyl group, nitro group, cyano group or monovalent, optionally substituted organic radical and
- $R_4$ denotes hydrogen, a halogen atom, nitro group, cyano group or monovalent, optionally substituted organic radical and
- $R_5$ can be identical or different and denotes a halogen atom, hydroxyl group, nitro group, cyano group or monovalent, optionally substituted organic radical and with the exception of

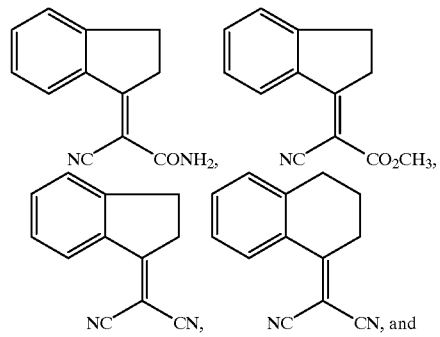

2. Process for the preparation of the compounds according to claim 1, which comprises condensing compounds of the formula

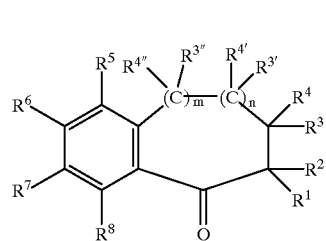

(II)

with compounds of the formula

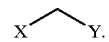

(III)

* * * * *